United States Patent
Viens et al.

(10) Patent No.: US 12,239,829 B2
(45) Date of Patent: Mar. 4, 2025

(54) MULTI-DOSE DISPENSER

(71) Applicant: DUOJECT MEDICAL SYSTEMS INC., Bromont (CA)

(72) Inventors: Mathieu Viens, Granby (CA); Robert Liddell, Granby (CA)

(73) Assignee: DUOJECT MEDICAL SYSTEMS INC., Bromont (CA)

( * ) Notice: Subject to any disclaimer, the term of this patent is extended or adjusted under 35 U.S.C. 154(b) by 708 days.

(21) Appl. No.: 17/300,646

(22) PCT Filed: Mar. 10, 2020

(86) PCT No.: PCT/CA2020/000023
§ 371 (c)(1),
(2) Date: Sep. 10, 2021

(87) PCT Pub. No.: WO2020/181357
PCT Pub. Date: Sep. 17, 2020

(65) Prior Publication Data
US 2022/0323687 A1 Oct. 13, 2022

(51) Int. Cl.
*A61M 5/315* (2006.01)
(52) U.S. Cl.
CPC .... *A61M 5/31593* (2013.01); *A61M 5/31526* (2013.01); *A61M 2005/31508* (2013.01)
(58) Field of Classification Search
CPC ........ A61M 2005/31508; A61M 5/315; A61M 5/31501; A61M 5/31511; A61M 5/31515; A61M 5/31525; A61M 5/31526; A61M 5/31533; A61M 5/31535; A61M 5/31545; A61M 5/31548; A61M 5/31555; A61M 5/31565; A61M 5/31576; A61M 5/31578; A61M 5/3158; A61M 5/3159; A61M 5/31593; A61M 5/31595
See application file for complete search history.

(56) References Cited

U.S. PATENT DOCUMENTS

2019/0060576 A1\* 2/2019 Kwolek ............ A61M 5/31515

\* cited by examiner

*Primary Examiner* — Shefali D Patel
(74) *Attorney, Agent, or Firm* — MEDLER FERRO WOODHOUSE & MILLS PLLC

(57) ABSTRACT

A multi-dose dispenser comprising an inner housing (16) and an outer housing (12), the inner housing (16) being movable within the outer housing (12) for a defined distance, a plunger rod (20) comprising a shaft (66) mounted within the inner housing (16), the shaft (66) having a plurality of spaced apart teeth (68) formed on the shaft (66), an actuator (22) located at one end of the shaft (66), the inner housing (16) having at least one pawl (70) arranged to engage with the teeth (68), a syringe (74) mounted interiorly of the inner housing (16), the syringe (74) being arranged such that the shaft (66) engages with a plunger within the syringe (74), and a spring member (18), the spring member (18) being biased between the inner housing (16) and the outer housing (12).

5 Claims, 3 Drawing Sheets

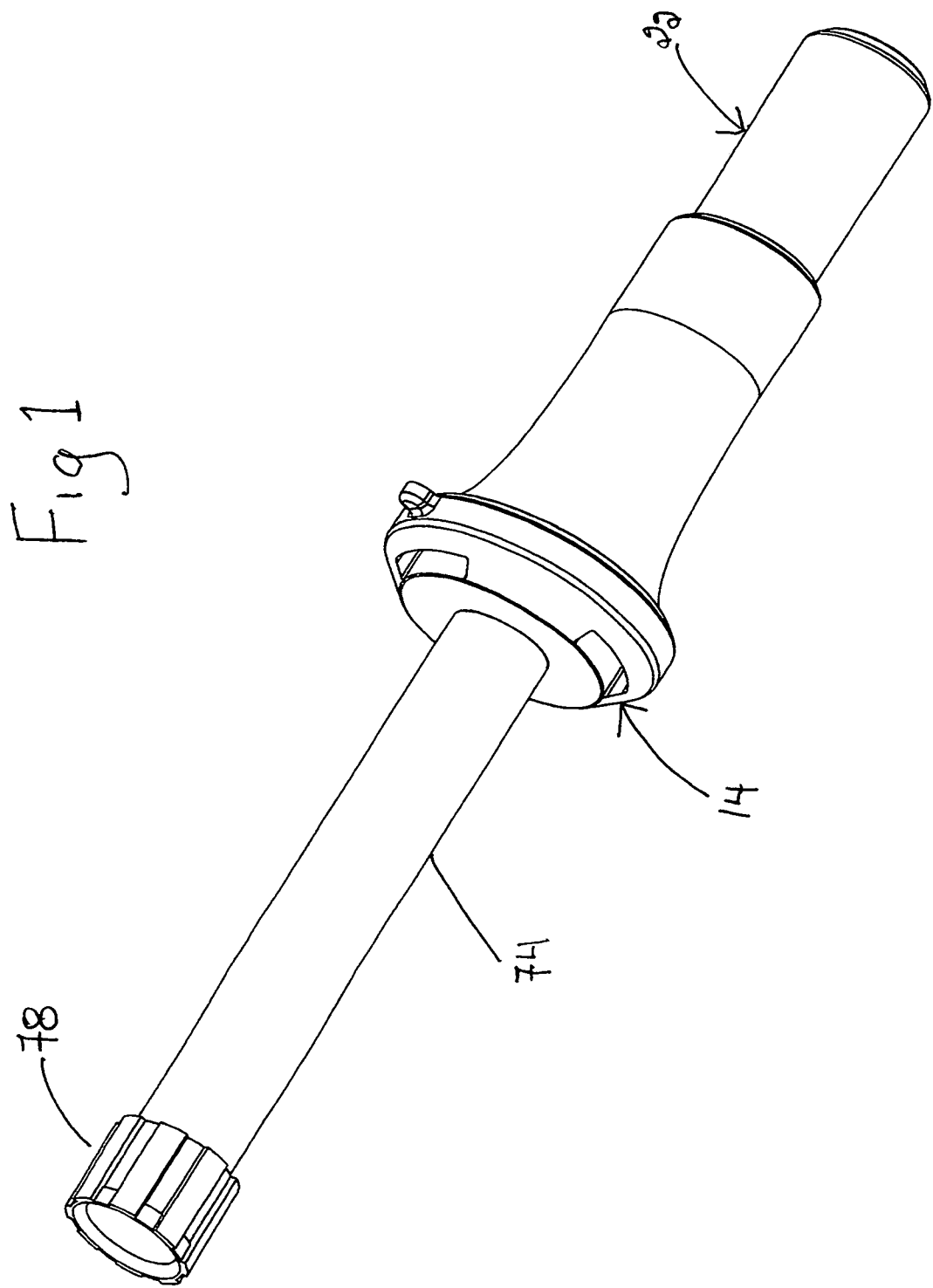

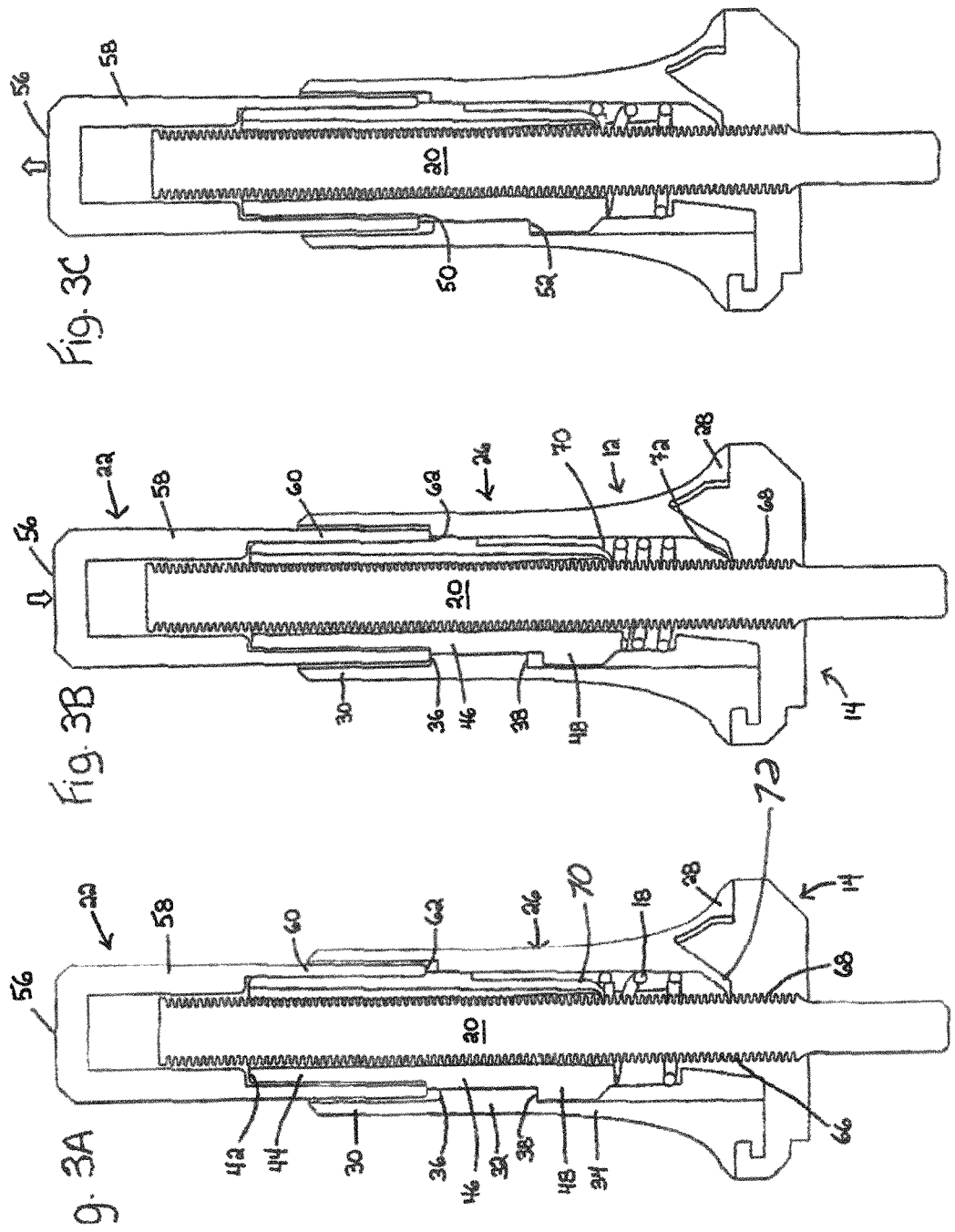

MULTI-DOSE DISPENSER

CROSS-REFERENCE TO RELATED APPLICATIONS

This application is a 371 of PCT/CA2020/000023, filed Mar. 10, 2020, and priority to CA 3,036,423, filed Mar. 11, 2019.

FIELD OF THE INVENTION

The present invention relates to an injection device and more particularly, relates to a multiple-dose injection device.

BACKGROUND OF THE INVENTION

Many different injection devices are known in the art; some such injection devices are designed to serve a particular purpose. One such specialized device is a multi-dose dispenser. In a multi-dose dispenser, very small amounts of a fluid are dispensed to a desired location. One of the uses of such a device would be in dispensing a drug such as Botox® which requires multiple small injections. A further use would be in dispensing a substance such as collagen which is injected under the skin. Naturally, there are other drugs which may also require repeated small doses such as aesthetic medication, dermal injections, etc.

One conventional device which is used is a cylindrical rectilinear syringe which comprises a cartridge containing the product along with a cylindrical and rectilinear rear plunger that is able to move within the cartridge. The operator simply pushes the plunger which slides inside the cartridge to eject the fluid through a needle mounted on the front end of the cartridge. This enables the person injecting the drug to control the amount injected by controlling the travel of the plunger. However, this is a very difficult procedure to master and it is virtually impossible to provide a precise dose utilizing such a device.

It has also been suggested in the art to attempt to control the injection by means of projections on the plunger which are used to limit the plunger travel and produce an audible sound once a given distance has been advanced. While this does provide some improvement, it also is subject to excessive pressure and therefore a variable dose. Furthermore, as the plunger rod and plunger advance, the position of the hand of the person giving the injection varies, making it difficult to control the pressure exerted on the plunger rod.

It has also been suggested to use an injector using a lever incorporating a pawl which acts as a rack.

Frequently, the lever is mounted on the side to advance the plunger rod. However, a disadvantage of such an arrangement is that the pressure exerted on the side will act to cause minor damage to the skin due to the transverse pressure rather than a straight linear movement.

SUMMARY OF THE INVENTION

It is an object of the present invention to provide a multi-dose dispenser which obviates the above problems.

According to one aspect of the present invention, there is provided a multi-dose injector comprising an inner housing and an outer housing, the inner housing being movable within the outer housing for a defined distance, a plunger rod comprising a shaft mounted within the inner housing, the shaft having a plurality of spaced apart teeth formed thereon, an actuator located at one end of the shaft, the inner housing having at least one pawl arranged to engage with the teeth, a syringe mounted interiorly of the inner housing, the syringe being arranged such that the shaft engages with a plunger within the syringe, and a spring member, the spring member being biased between the inner housing and the outer housing.

As aforementioned, the dispenser has an inner housing and an outer housing. The housings are mounted such that the inner housing is slidable within the outer housing; however the sliding movement is very limited and is defined by horizontal surfaces which abut each other to thereby limit the relative amount of movement. This small amount of movement controls the amount of the dose which is dispensed.

Mounted within the inner housing is a plunger rod which has a serrated shaft upon which there are formed a plurality of teeth. Preferably, each tooth is spaced equally from its neighbours. The dispenser includes a syringe which fits within the housings and which syringe is filled with the fluid which is to be dispensed. The syringe will, as is conventional, include a plunger therein. The serrated shaft is mounted so as to bear on the plunger.

The inner housing will include latches formed therein. Preferably, there are three latches surrounding the plunger rod. There are two sets of such latches; advancing latches and retaining latches.

BRIEF DESCRIPTION OF THE DRAWINGS

Having thus generally described the invention, reference will be made to the accompanying drawings illustrating an embodiment thereof, in which:

FIG. 1 is a perspective view illustrating the dispenser in a first position;

FIG. 3A is a sectional view illustrating a portion of the dispenser in a non-dispensing position;

FIG. 3B is a cross-sectional view illustrating the dispenser during dispensing of a dose; and FIG. 3C is a cross-sectional view during retraction of the plunger rod.

DETAILED DESCRIPTION OF THE INVENTION

Figure 2C:
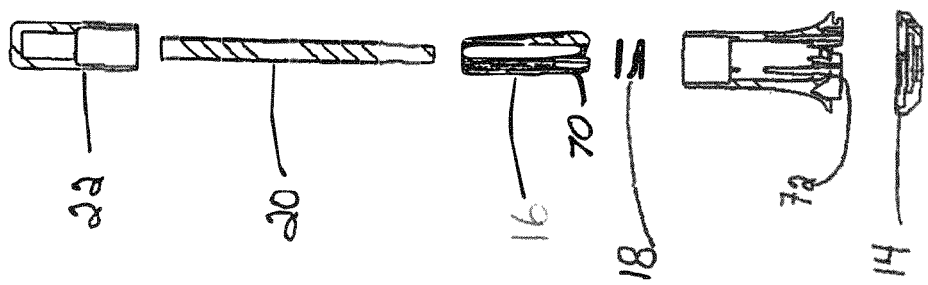
FIG. 2C is an exploded sectional view thereof.
Figure 2B:
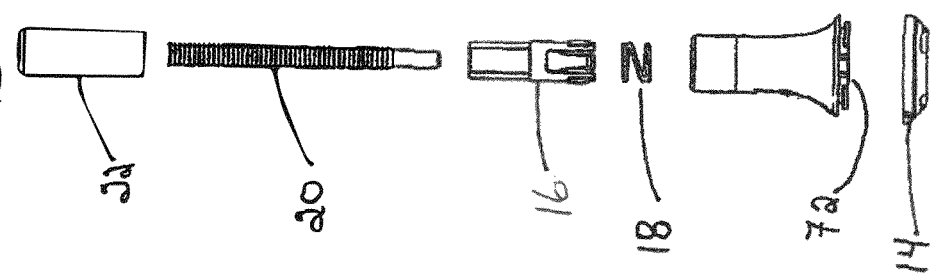
FIG. 2B is a an exploded view illustrating the dispenser which has been rotated.
Figure 2A:
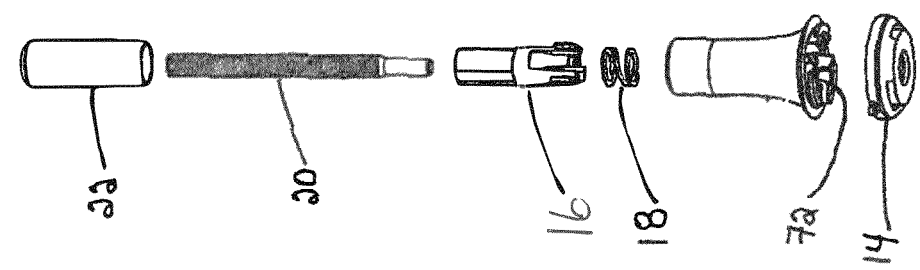
FIG. 2A is an exploded view of a portion of the dispenser.

Referring to the drawings in greater detail and by reference characters thereto, there is illustrated a multi-dose dispenser.

Multi-dose dispenser includes an outer housing 12, a cover 14, an inner housing 16, a coil spring 18, a plunger rod 20 and an actuator or push button 22.

Outer housing 12 has side wall 26 with a lower outwardly extending portion 28. Side wall 26 is formed of an upper wall segment 30, a middle wall segment 32 and a lower wall segment 34. As will be noted, middle wall segment 32 extends inwardly a greater distance than upper wall segment 30 or lower wall segment 34. As a result, a shoulder 36 is formed between upper wall segment 30 and middle wall segment 32 and abutment 38 is formed between middle wall segment 32 and lower wall segment 34.

Inner housing 16 has a top wall 42, an inner housing upper side wall 44, an inner housing middle side wall 46 and an inner housing lower side wall 48. The wall segments are of different thicknesses with inner housing upper side wall 44 having the thinnest profile and inner housing lower side wall 48 having the thickest profile.

As shown in FIG. 3C, a shoulder 50 is formed between inner housing upper side wall 44 and inner housing middle side wall 46. An abutment 52 is formed between inner housing middle side wall 46 and inner housing lower side wall 48.

An actuator or push button 22 has a button top wall 56, a button upper side wall 58, a button lower side wall 60 and a button bottom wall 62.

Mounted within inner housing 16 is plunger rod 20 which comprises a serrated shaft 66 having a plurality of teeth 68 on the exterior thereof. Each tooth 68 is equidistantly spaced from its adjacent teeth.

Outer housing 12 includes an advancing latch or pawl 70 and a retaining latch or pawl 72.

As shown in FIG. 1, the multi-dose dispenser also includes a syringe 74 having a plunger mounted therein. A plunger is operatively connected to plunger rod 20 in a conventional manner. Syringe 74 has a dispensing end 78 which may terminate with any suitable device such as a needle or other dispenser.

In operation, push button 22 is engaged with top wall 42 of inner housing 16 to advance the same downwardly. With the movement of inner housing 16, a gap is formed between abutment 38 and abutment 52. The downward movement of inner housing 16 will also cause advancing latch 70 to push on plunger rod 20 to also advance the same downwardly. During this movement, retaining latch 72 is forced outwardly and spring 18 is compressed. At this point in time, inner housing 16 cannot advance any further due to engagement of button bottom wall 62 with shoulder 36.

As a result, pressure may be released on push button 22 and spring 18, which has been compressed, and will act to drive inner housing 16 upwardly to be in position for the next push.

This sequence is repeated for each dose required. As shown in FIG. 1, the advancement of plunger rod 20 will act to move the plunger and force fluid through dispensing end 78.

It will be understood that the particular fluid within syringe 74 may be selected from any desired. The fluid may be a liquid or paste as desired.

The inner housing in the illustrated embodiment has three spaced apart advancing and retaining latches; it will be understood that more or fewer may be used.

It will be understood that the above-described embodiments are for purposes of illustration only and that changes and modifications may be made thereto without departing from the spirit and scope of the invention.

We claim:

1. A multi-dose dispenser comprising:
   an inner housing (16) and an outer housing (12), said inner housing (16) being movable within said outer housing (12) for a defined distance;
   a plunger rod (20) comprising a shaft (66) mounted within said inner housing (16), said shaft (66) having a plurality of spaced apart teeth (68) circling said shaft (66) formed on said shaft (6);
   an actuator (22) located at one end of said shaft (66) for advancing the inner housing (16) said defined distance between an original position and an advanced position;
   said inner housing (16) having at least one pawl (70) arranged to engage with said teeth (68);
   a syringe (74) co-axially mounted interiorly of said inner housing (16), said syringe (74) being arranged such that said shaft (66) engages with a plunger within said syringe (74); and
   a spring member (18), said spring member (18) being biased between said inner housing (16) and said outer housing (12);
   wherein the outer housing (12) has a shoulder (36) and the actuator (22) has a button bottom wall (62);
   and wherein when the actuator (22) is engaged, the inner housing (16) and the shaft (66) are advanced together from the original position to the advanced position through engagement of the button bottom wall (62) with the shoulder (36);
   and wherein the inner housing (16) and the shaft (66) are returned to the original position from the advanced position by force of the spring member (18) when the actuator (22) is released.

2. The multi-dose dispenser of claim 1 wherein said spring member (18) comprises a coil spring.

3. The multi-dose dispenser of claim 2 wherein the actuator (22) engages with said inner housing (16) to advance said inner housing (16) in a first direction, the at least one pawl (70) of said inner housing (16) engaging said shaft (66) to drive said shaft (66) in said first direction.

4. The multi-dose dispenser of claim 3 wherein said outer housing (12) has a pawl (72) adapted to retain said shaft (66) in position after advancing movement of said shaft (66) in said first direction.

5. The multi-dose dispenser of claim 4 wherein said spring member (18) is operative to return said inner housing (16) to the original position upon release of pressure from said actuator (22).

* * * * *

UNITED STATES PATENT AND TRADEMARK OFFICE
CERTIFICATE OF CORRECTION

PATENT NO. : 12,239,829 B2
APPLICATION NO. : 17/300646
DATED : March 4, 2025
INVENTOR(S) : Mathieu Viens and Robert Liddell Page 1 of 1

It is certified that error appears in the above-identified patent and that said Letters Patent is hereby corrected as shown below:

In the Claims

Column 4, Line 9, Claim 1:
Replace "formed on said shaft (6);" with --formed on said shaft (66);--

Signed and Sealed this
First Day of April, 2025

Coke Morgan Stewart
*Acting Director of the United States Patent and Trademark Office*